United States Patent
Hanreich et al.

(10) Patent No.: US 11,053,487 B2
(45) Date of Patent: Jul. 6, 2021

(54) ARABINANASE AND USES THEREOF

(71) Applicant: BIOPRACT GMBH, Berlin (DE)

(72) Inventors: Angelika Hanreich, Berlin (DE); Joachim Pheiffer, Berlin (DE); Sebastian Worch, Halle/Saale (DE); Gotthard Kunze, Seeland (DE); Tobias Schwalenberg, Bernburg (DE); Reinhard Patz, Kothen/Anhalt (DE)

(73) Assignee: BIOPRACT GMBH, Berlin (DE)

( * ) Notice: Subject to any disclaimer, the term of this patent is extended or adjusted under 35 U.S.C. 154(b) by 67 days.

(21) Appl. No.: 16/104,911

(22) Filed: Aug. 19, 2018

(65) Prior Publication Data
US 2018/0355334 A1 Dec. 13, 2018

Related U.S. Application Data

(63) Continuation of application No. PCT/EP2017/053672, filed on Feb. 17, 2017.

(30) Foreign Application Priority Data

Feb. 18, 2016 (EP) ..................................... 16156338
Aug. 15, 2016 (EP) ..................................... 16184187

(51) Int. Cl.
*C12N 9/24* (2006.01)
*A23K 50/30* (2016.01)
(Continued)

(52) U.S. Cl.
CPC ............ *C12N 9/2402* (2013.01); *A23K 10/12* (2016.05); *A23K 10/14* (2016.05); *A23K 50/30* (2016.05);
(Continued)

(58) Field of Classification Search
CPC ........ C12N 9/24; C12N 9/2402; A23K 50/30; A23K 50/75; A23K 10/14; A23K 10/12; C12Y 302/01099; C12Y 302/01055
See application file for complete search history.

(56) References Cited

U.S. PATENT DOCUMENTS

| | | | | |
|---|---|---|---|---|
| 5,718,894 | A * | 2/1998 | Mann | A61K 35/742 424/93.3 |
| 2011/0287135 | A1* | 11/2011 | Kuehnel | C07H 21/00 426/15 |
| 2014/0329283 | A1* | 11/2014 | Sorensen | C12N 9/244 435/93 |

FOREIGN PATENT DOCUMENTS

WO   WO-2015097017 A1 *   7/2015   ..... C12Y 302/01099

OTHER PUBLICATIONS

Park et al. J. Microbiol. Biotechnol. (2015),25(2), 227-233 (Year: 2015).*

(Continued)

*Primary Examiner* — Subbalakshmi Prakash
(74) *Attorney, Agent, or Firm* — JMB Davis Ben-David (57) ABSTRACT

The invention relates to the use of an isolated arabinanase enzyme comprising the activities of (1-5)-α-arabinofuranosidic linkage endohydrolysis in (1-5)-α-L-arabinans (EC 3.2.1.99), and hydrolysis of (1-5)-α-arabinofuranosidic linkages at the non-reducing end of α-L-arabinans or α-L-arabinose-oligomers (EC 3.2.1.55), particularly an arabinan-degrading enzyme isolated from *Arxula adeninivorans* as feed additive in livestock breeding. Furthermore, the invention relates to the application of the arabinanase in the production of fruit juices or biofuels.

14 Claims, 4 Drawing Sheets

Specification includes a Sequence Listing.

(51) Int. Cl.
*A23K 50/75* (2016.01)
*A23K 10/12* (2016.01)
*A23K 10/14* (2016.01)

(52) U.S. Cl.
CPC ............... *A23K 50/75* (2016.05); *C12N 9/24* (2013.01); *C12Y 302/01055* (2013.01); *C12Y 302/01099* (2013.01)

(56) References Cited

OTHER PUBLICATIONS

International Preliminary Report on Patentability (Chapter I of the Patent Cooperation Treaty), dated Aug. 21, 2018 (Year: 2018).*

* cited by examiner

ARABINANASE AND USES THEREOF

CROSS-REFERENCE TO RELATED APPLICATIONS

This is a Continuation of International Patent Application No. PCT/EP2017/053672 filed on Feb. 17, 2017, which was published in English under PCT Article 21(2), which in turn claims the benefit of European Patent Application Nos. 16156338.2 filed on Feb. 18, 2016 and 16184187.9 filed Aug. 15, 2016. The foregoing patent applications are incorporated by reference herein in their entirety.

FIELD

The present invention relates to hydrolytic enzymes with arabinanase activity and their use as feed additive in livestock breeding.

BACKGROUND OF THE INVENTION

Arabinan is a neutral polysaccharide that mainly occurs as side chain of pectin. A linear α-L-arabinan consists of a backbone of arabinose monomers linked by α-1,5-glycosidic (arabinofuranosidic) bonds. In a branched α-L-arabinan, arabinose monomers or arabinose oligomers are linked to the backbone via α-1,2- or α-1,3-glycosidic (arabinofuranosidic) bonds.

Arabinanases are hydrolytic enzymes capable of cleaving arabinan. Endo-arabinanases (EC 3.2.1.99) hydrolyze α-1,5-glycosidic bonds within the linear backbone of α-L-arabinans. α-L-arabino-furanosidases (EC 3.2.1.55) hydrolyze α-1,5- and/or α-1,3- and/or α-1,2-glycosidic bonds at the non-reducing end of α-L-arabinans or α-L-arabinose-oligomers, thereby releasing arabinose monomers.

Rapeseed meal (RSM) and soybean meal (SBM) are byproducts of bioethanol and food production. They are inexpensive, available on a large scale, and have a high protein content. For these reasons, they are often used as feed ingredients for poultry and pigs. They contain many non-starch polysaccharides (NSPs), mainly pectin, that can only partly be digested by the animals. For poultry, the digestability of NSPs from rapeseed meal and soybean meal is 14% and 20%, respectively. Pigs are able to digest 58% of NSPs from rapeseed meal and 84% of NSP from soybean meal. The degree of digestion of substrates also differs between animals of different age. Especially young animals cannot sufficiently use carbohydrates present in the diet, which has negative effects on growth performance (antinutritive effect).

If a feed ingredient is only partly digested, not all energy contained in the feed ingredient is utilized. In addition, undigested NSPs have an effect on the viscosity of the feed within the digestive tract. Fluidity is enhanced, resulting in an impaired digestibility of other nutrients.

To improve digestion of NSPs, feed ingredients or compound feed can be pretreated mechanically, thermally or enzymatically.

The use of enzymes in livestock feeding was established in the 1980s. Prevalent enzyme preparations added to feed comprise cellulase, xylanase, glucanase and/or pectinase activity. Some preparations contain several enzyme activities (multi component preparations), others contain only one (single component preparations).

WO 1992017592 A1 ("Cloning and expression of DNA molecules encoding arabinan-degrading enzymes of fungal origin) describes cloning of a fungal arabinanase and its use in production of fruit and vegetable juice.

WO 1994020611 A1 ("An enzyme with arabinanase activity") describes an enzyme preparation enriched in an arabinanase from *Aspergillus aculeatus*.

WO 1995029598 A1 ("Enzymatic treatment of soy)" describes an enzyme mixture comprising several enzyme activities (including an endo-arabinanase of fungal origin) for the treatment of an aqueous suspension of soy meal.

US 2011/0287135 ("Novel arabinohydrolases") describes a multi-enzyme composition comprising several enzymes with arabinanase activity for hydrolyzing arabinans present in plant biomass.

The problem underlying the present invention is to improve the digestability of pectin-rich feed ingredients or mixed feed. The problem is solved by the subject-matter of the independent claims.

SUMMARY

A first aspect of the invention relates to an isolated enzyme having arabinanase activity and the use of an isolated enzyme having arabinanase activity. The arabinase activity is characterized in that it comprises the activities of
 a. endohydrolysis of (1-5)-α-arabinofuranosidic linkages in (1-5)-α-L-arabinans (EC 3.2.1.99), and
 b. hydrolysis of (1-5)-α-arabinofuranosidic linkages at the non-reducing end of α-L-arabinans or α-L-arabinose-oligomers (EC 3.2.1.55).

DETAILED DESCRIPTION

Figure 1:
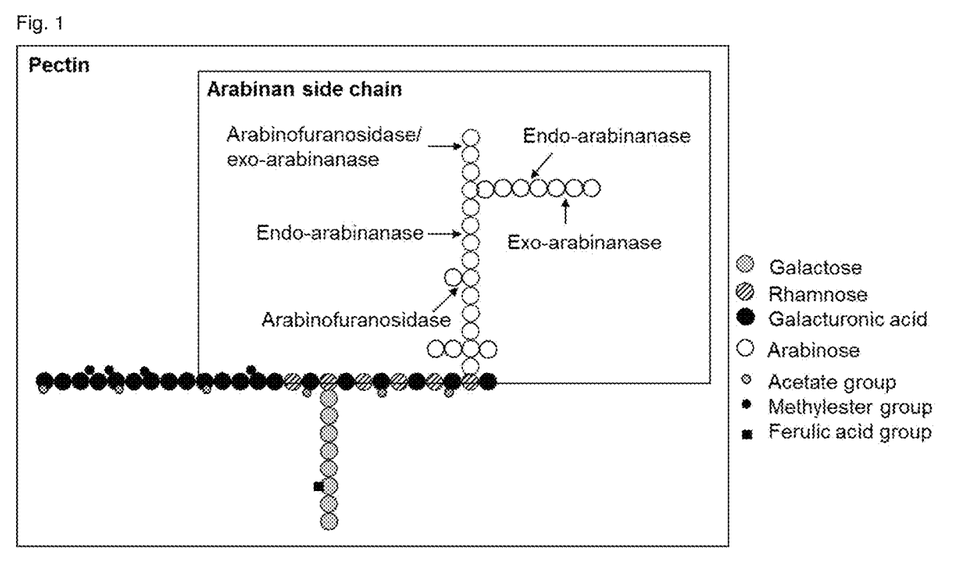
FIG. 1 shows a schematic drawing of arabinan.

Within the context of the present specification, the term "arabinan" signifies a polysaccharide comprising a backbone of arabinose monomers linked by α-1,5-glycosidic bonds. In a branched arabinan, arabinose monomers or arabinose oligomers are linked to the backbone via α-1,2- and/or α-1,3-glycosidic bonds (FIG. 1).

Within the context of the present specification, the term "enzyme" signifies a single protein consisting of a single amino acid chain.

Within the context of the present specification, the term "isolated enzyme" signifies that said enzyme was intentionally produced/isolated and is not a random, minor or negligible component or byproduct.

The enzyme having arabinanase activity according to the present invention is able to degrade arabinan from the reducing end (arabinofuranosidase activity) and from within the arabinan chain (endoarabinanase activity). It is thus bifunctional.

In certain embodiments, the enzyme is characterized by an amino acid sequence exhibiting at least 55%, 60%, 65%, 70%, 75%, 80%, 85%, 90%, 92%, 94%, 96%, 98%, 99% or 100% identity with SEQ ID NO 02.

The enzyme according to the present invention was amplified from *A. adeninivorans* genomic DNA.

In certain embodiments, the enzyme additionally catalyses hydrolysis of (1-3) and/or (1,2)-α-arabinofuranosidic linkages at the non-reducing end of α-L-arabinans or α-L-arabinose-oligomers.

The presence of both endoarabinanase activity and arabinofuranosidase activity has the advantage that branched arabinan can be degraded more efficiently. The arabinofuranosidase activity degrades the arabinose oligomers linked to the arabinan backbone and removes the arabinose monomers linked to the arabinan backbone (debranching). In parallel, the linear backbone is degraded by the endoarabinanase activity (depolymerization). Endoarabinanase activity is known to be inhibited the presence of arabinan oligomers. Due to the arabinofuranosidase activity, the oligomers produced during the depolymerization are degraded. The dual activity of the enzyme according to the present invention thus results in a complete and efficient degradation of arabinan.

The enzyme exhibits optimum activity at a temperature between 40° C. and 55° C. The enzyme exhibits optimum activity at a pH between 3.5 and 5.5.

Without further formulation, the enzyme according to the present invention is thermostable up to a temperature of approx. 65° C. During incubation at 60° C. for 2 hours, enzymatic activity does not decrease. This signifies an improved thermo-stability compared to the arabinanase isolated from *Aspergillus aculeatus* (WO 1994020611 A1), which is partly inhibited at 50° C. The enzyme according to the present invention is also stable between pH 3 and pH 9 and at a salt concentration from 50-100 mmol/l.

These properties enable the generation of feed comprising the enzyme according to the present invention. The arabinanase activity can be further protected, e.g. by a heat protective coating that prevents loss of enzyme activity during pelletizing.

The enzyme according to the present invention is active under the environmental conditions within the digestive tract.

Another aspect of the invention relates to the use of the isolated enzyme according to any embodiment of the first aspect of the invention for the degradation of plant biomass or for the preparation of a feedstock additive. In certain embodiments of this aspect of the invention, the plant biomass is a pectin-rich plant biomass.

In certain embodiments of this aspect of the invention, a feedstock additive is prepared and used in livestock feeding.

In certain embodiments of this aspect of the invention, the plant biomass is a liquid preparation comprising pectin-containing plant material, in particular apple juice, pear juice, grape juice, orange juice, lemon juice, tomato juice, or carrot juice. The use of the isolated enzyme for the degradation of plant biomass comprises contacting the liquid preparation with the enzyme.

In certain embodiments of this aspect of the invention, the degradation of plant biomass relates to improved degradation of substrates for biofuel production, particularly biogas and bioethanol production.

Another aspect of the invention relates to an isolated nucleic acid sequence. This nucleic acid sequence from which the enzyme for carrying out the present invention can be expressed a. encodes the enzyme according to the first aspect of the invention; and/or
b. comprises or essentially consists of the nucleic acid sequence specified by SEQ ID NO 01; and/or
c. comprises a sequence of at least 750, 800, 850, 900, 950, 1000, 1050, 1100 or 1150 basepairs able to hybridize to SEQ ID NO 01 under high stringency conditions.

In the context of the present specification, the term "high stringency conditions" relates to hybridization conditions that require essentially all bases of a polynucleotide of 500 bp length to be paired with complementary bases of the other polynucleotide.

Another aspect of the invention relates to a recombinant expression vector, from which the enzyme for carrying out the present invention can be expressed. This vector comprises the nucleic acid sequence as laid out above, wherein said nucleic acid sequence is operably linked to a regulatory element facilitating the expression of the nucleic acid sequence in a host cell.

Another aspect of the invention relates to a cell comprising the aforementioned nucleic acid sequence or the aforementioned recombinant expression vector.

In certain embodiments of this aspect of the invention, the cell is a prokaryotic cell, particularly a cell belonging to the genus of *Escherichia* or *Bacillus*.

In certain embodiments of this aspect of the invention, the cell is a eukaryotic cell, particularly a filamentous fungus or a yeast cell. The filamentous fungus may be selected from an *Aspergillus* ssp. cell, particularly an *Aspergillus oryzea* cell or an *Aspergillus niger* cell, or from an *Trichoderma* ssp cell, particularly a *Trichoderma reesei* cell. The yeast cell may be selected from an *Arxula adeninivorans* cell, a *Hansenula polymorpha* cell, a *Pichia* ssp. cell, particularly a *Pichia pastoris* cell or a *Saccharomyces cerevisiae* cell.

Another aspect of the invention relates to a method of synthesis of the enzyme for carrying out the invention. A method of synthesis of the enzyme for carrying out the invention comprises the steps of a. providing a cell culture comprising cells, particularly yeast cells, particularly *Arxula adeninivorans* or *Hansenula polymorpha*, wherein said cells comprise a recombinant expression vector comprising a DNA sequence encoding said enzyme,
b. fermenting said cells in a fed-batch procedure, and
c. purifying the enzyme from the cell culture.

In certain embodiments of this aspect of the invention, the cells are selected from *Arxula adeninivorans* or *Hansenula polymorpha*.

In certain embodiments of this aspect of the invention, the fed-batch procedure comprises a batch phase and a feed phase, wherein the feed phase is performed at pH 6 and $pO_2$ 40%.

According to yet another aspect of the invention, a single component enzyme preparation comprising an enzyme having arabinanase activity is provided. The arabinanase activity catalyses a. endohydrolysis of (1-5)-α-arabinofuranosidic linkages in (1-5)-α L arabinans (EC 3.2.1.99), and
b. hydrolysis of (1-5)-α-arabinofuranosidic linkages at the non-reducing end of α-L-arabinans or α-L-arabinose-oligomers (EC 3.2.1.55).

In the context of the present specification, the term "single component enzyme preparation" signifies an enzyme preparation essentially containing a single enzyme.

The single component enzyme preparation according to the present invention essentially contains a single bifunctional enzyme. One advantage of using a "single component enzyme preparation" containing a bifunctional enzyme rather than a multicomponent enzyme preparation is that production of a single enzyme preparation is faster and more cost-efficient. The parameters for production and use can be optimized much easier. In addition, registration of multi-component enzyme preparations for use as feed additive is much more complex and challenging than registration of a single component enzyme preparation.

In certain embodiments of this aspect of the invention, the enzyme having an arabinanase activity is characterized by the amino acid sequence of SEQ ID NO 02 or by an amino acid sequence exhibiting at least 55%, 60%, 65%, 70%, 75% 80%, 85%, 90%, 92%, 94%, 96%, 98%, 99% or 100% identity with SEQ ID NO 02.

In certain embodiments of this aspect of the invention, the arabinanase activity additionally catalyses hydrolysis of (1-3)-α- and/or the (1-2)-α-arabinofuranosidic linkages at the non-reducing end of α-L-arabinans or α-L-arabinose-oligomers.

According to yet another aspect of the invention, the use of the isolated enzyme according to any embodiment of the first aspect of the invention is provided for the manufacture of a single component enzyme preparation for the degradation of plant biomass or for the preparation of a feedstock additive. In certain embodiments of this aspect of the invention, the plant biomass is a pectin-rich plant biomass.

According to another aspect of the invention, a process for the degradation of plant biomass is provided. The process comprises the steps of
 a. providing an aqueous preparation of a plant biomass, particularly selected from a liquid preparation comprising pectin-containing plant material, in particular apple juice, pear juice, grape juice, orange juice, lemon juice, tomato juice, or carrot juice, or a substrate for biofuel production, then
 b. adding an isolated enzyme having arabinanase activity as specified herein,
 c. reacting said aqueous preparation of a plant biomass in the presence of said isolated enzyme at a temperature of between 35° C. and 60° C., particularly between 40° C. and 55° C., and at a pH between 3.5 and 5.5, and
 d. collecting the degradation product from said process.

According to yet another aspect of the invention, a compound feed is provided, comprising or essentially consisting of
 a. a pectin-rich biomass and
 b. a single component enzyme preparation as specified in the respective aspect of the invention.

In the context of the present specification, the term "compound feed" relates to an animal feed comprising multiple components. Non-limiting examples for such components are carbohydrate containing components, protein containing components and feed additives such as vitamins or enzyme preparations.

In the context of the present invention, the term "pectin-rich biomass" relates to a biomass in which the cell walls contain more than 12% pectin on a dry weight basis. Non-limiting examples of pectin-rich biomass are soybean and soybean meal (SBM), lupins, rapeseed, rapeseed meal (RSM), other oilseeds and legumes and sugar beet.

In certain embodiments, the compound feed comprises 5%-50% (w/w), particularly 15%-25% (w/w) of a pectin-rich biomass.

According to an alternative of the above aspect of the invention, a compound feed is provided that comprises a pectin-rich biomass and a single component enzyme preparation as specified in the respective aspect of the invention, and additionally comprises another feed component, particularly a starch-bearing feed component such as grain or maize.

In other words, the invention provides a compound feed having a significant percentage of pectin-rich biomass and a single enzyme preparation added to facilitate utilization of the pectin component. The pectin and arabinanase components may be pelleted individually, or together with conventional compound feed components that are rich in starch (wheat, maize) and typically constitute between 50% and 95% of the compound feed fed to a farm animal.

The use of the enzyme according to the present invention as feed additive improves the digestability of pectin-rich foodstuff like soybean and soybean meal (SBM), lupins, rapeseed, rapeseed meal (RSM), other oilseeds and legumes and sugar beet.

Surprisingly, the inventors found that addition of the highly active, bifunctional arabinanase according to the present invention is able to improve the degradation of pectin-rich feed ingredients like soybean meal or rapeseed meal to an unexpected extent. The arabinanase acts exclusively on arabinan. It releases arabinose-polymers, -oligomers and -monomers, which can be further exploited. In addition, fluidity of the feed is improved. The observed effect is surprising, since the enzyme does not act on the pectin backbone which consists mainly of polygalacturonan. Pectinase preparations like Ronozyme VP (DSM) mainly act on the pectin backbone.

Unexpectedly, the arabinanase according to the present invention is faster and more efficient than comparable pectinase preparations in releasing arabinose-oligomers and/or -monomers from naturally occurring polymers. A fast effect of feed additives is advantageous, since the retention time within the intestinal tract is only 4 to 8 hours for poultry and other monogastric animals (Enzyms in farm animal nutrition, $2^{nd}$ edition, Bedford and Partridge, 2010).

In certain embodiments of this aspect of the invention, the concentration of said enzyme preparation is is 1-500 mg/kg, particularly 10-400 mg/kg, more particularly 100-300 mg/kg.

In certain embodiments of this aspect of the invention, the pectin-rich biomass is selected from sugar beet, oilseed and legume, more particularly rapeseed, rapeseed meal, lupins, soybean and soybean meal.

In certain embodiments of this aspect of the invention, the compound feed further comprises an additional isolated enzyme, particularly phytase, protease and/or NSP-degrading enzyme at a concentration of 1-500 mg/kg, even more particularly 10-400 mg/kg, even more particularly 100-300 mg/kg.

In certain embodiments of this aspect of the invention the compound feed comprises two isolated enzymes, selected from:
 a. the enzyme according to the first aspect of the invention and a phytase;
 b. the enzyme according to the first aspect of the invention and an NSP-degrading enzyme, particularly a pectinase; and
 c. the enzyme according to the first aspect of the invention and a protease, particularly an acid stable serine protease.

Synergistic effects of arabinanase and phytase have been shown in poultry diets. Without wanting to be bound by theory, the inventors believe that the partial degradation of pectin by arabinanase reduces the antinutritive effect of this particular NSP-fraction and increases the apparent metabolizable energy. Hydrolysis of arabinan side chains may also facilitate the degradation of phytate, which becomes more accessible, by the supplemented phytase resulting in a higher release of phosphorus and complexed trace elements. The presence of trace elements might also increase the activity of arabinanase, which was shown in prior lab experiments.

Figure 3:
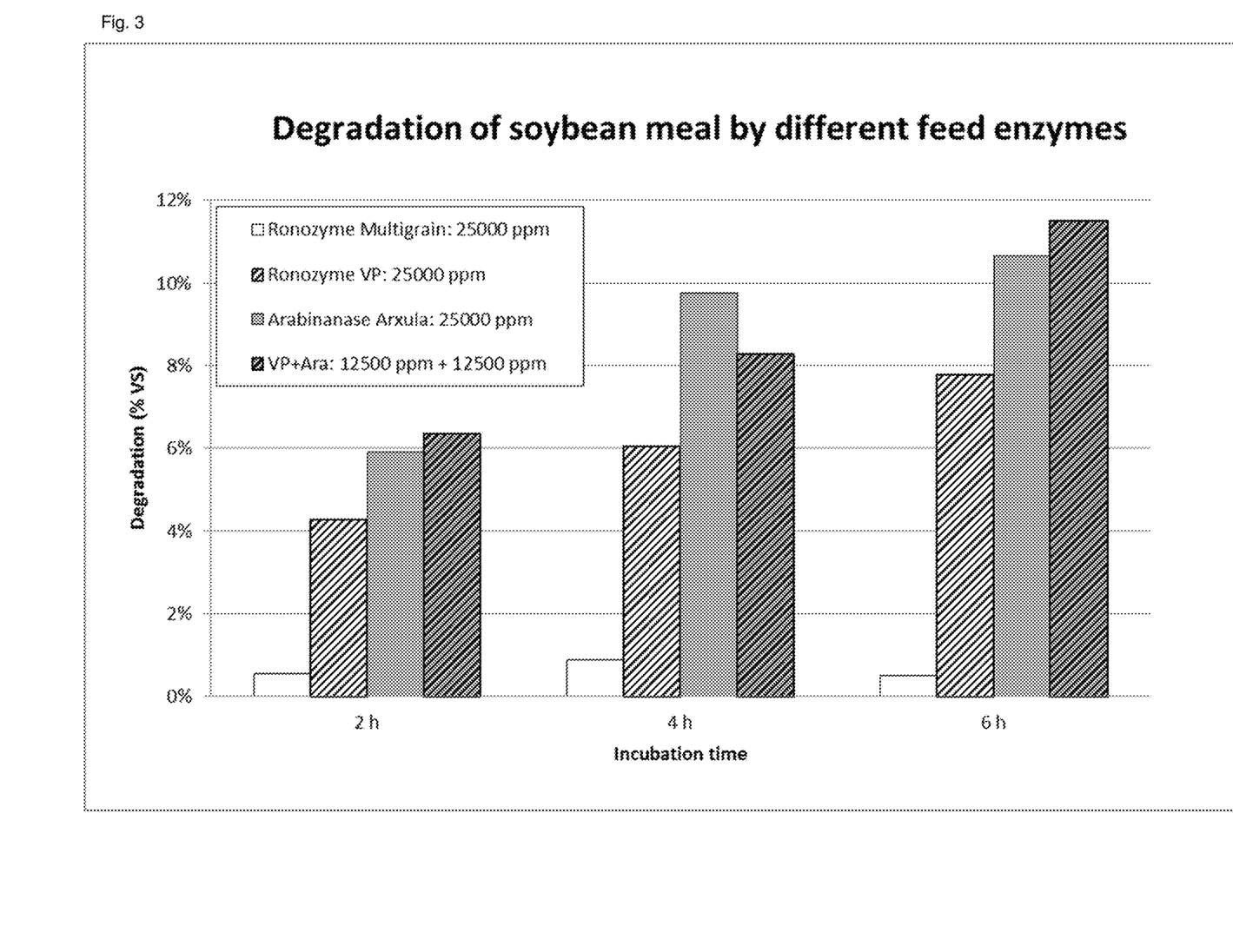
FIG. 3 shows the degradation of soybean meal by the arabinanase according to the present invention and by established feed additives.
Figure 4:
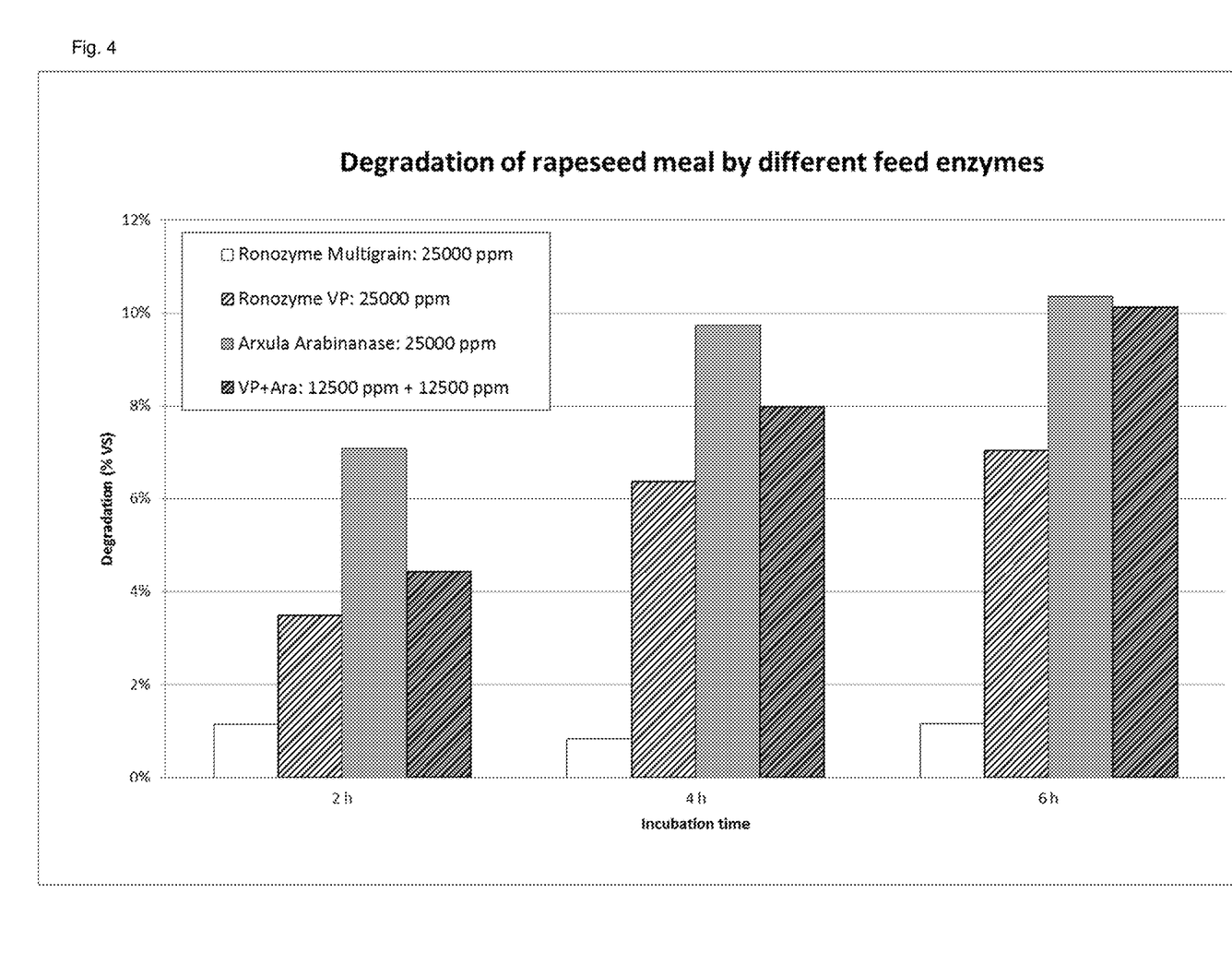
FIG. 4 shows the degradation of rapeseed meal by the arabinanase according to the present invention and by established feed additives.

The supplementation of arabinanase and NSP-degrading enzymes, in particular a pectinase, shows synergistic effects in poultry diets. The advantages of both enzymes, i.e. the fast depolymerization of side chains by the arabinanase and the efficient degradation of the pectin backbone by a pectinase, lead to a reduction of antinutritive effects in NSP-rich diets and to an increase of apparent metabolizable energy (FIGS. 3 and 4).

Synergistic effects of protease and arabinanase have been shown in poultry diets. The partial degradation of pectin by arabinanase reduces the antinutritive effect of this particular NSP-fraction. The degaration of arabinan side chains facilitate the access to proteins, which are partly encaged by pectins and fiber. The breakdown of before inaccessible proteins is catalyzed by the protease leads to a higher release of peptides and amino acids. It seems as if the apparent metabolizable energy is increased strongly by the combined approach.

According to yet another aspect of the invention, a use of the compound feed described above in livestock feeding is provided. The livestock is selected from monogastric animals, particularly poultry or pigs, more particularly poultry selected from chicken, duck and turkey.

According to yet another aspect of the invention, the enzyme as specified according to any one of the above aspects or embodiments of the invention is used for treating pectin containing plant material, such as fruits and vegetables.

Certain embodiments of this aspect provide a process for treatment of a fruit mash or a liquid preparation comprising pectin containing plant material. The process comprises contacting a mash or liquid preparation of a plant material with an isolated arabinanase enzyme as specified in the first aspect of the invention, or a preparation thereof. In certain embodiments, the arabinanase preparation, which can also contain cellulases, glucanases, amylases and/or pectinases, is used for improvement of extractability and degradation of mash from fruit and vegetables. The enzyme or the enzyme preparation is added to the fruit mash and incubated for 1-5 hours at temperatures between 10° C. and 25° C. in concentrations of 10-400 mg/kg, even more particularly 100-300 mg/kg mash. After enzymatic pretreatment, juice is pressed out of the mash. In certain embodiments, the arabinanase preparation is used for viscosity reduction, especially in apple or pear juice. In certain embodiments, the arabinanase preparation is used for prevention of haze production. Arabinanase or arabinanase preparations are added to hazy juice, which have pH values between 3 and 4.5, at temperatures between 10° C. and 25° C. in concentrations of 10-400 mg/kg, even more particularly 100-300 mg/kg juice and incubated for 1 to 5 hours. Juices are then cleared by the addition of diatomite, bentonite or other additives and filtered. The resulting clear juices are preserved by pasteurization.

In certain embodiments, the liquid preparation of plant material is fruit juice, particularly juice from apples, pears or grapes. In certain embodiments, the liquid preparation of plant material is vegetable juice, particularly juice from tomatoes or carrots.

Consistency and appearance of fruit juices may be adapted. Products with specific properties, such as clear juice, cloud stable juice or purees from fruits and vegetables, e.g. apple, berries, grape, citrus, tomatoes or carrots, may be produced using the arabinanase of the invention alone or in combination with other enzymes, such as cellulases, glucanases, pectinases and/or amylases.

According to yet another aspect of the invention, the enzyme as specified according to any one of the above aspects or embodiments of the invention is used for treating pectin containing plant material, such as sugar beets, whole plant silages, fruit or other arabinan-containing organic substrates during biofuel production. Biofuel production includes the production of bioethanol or biogas.

The production of bioethanol can be enhanced by pretreating pectin-rich biomass, such as sugar beet, fruit, fruit mash and other pectin-containing substrates with the arabinanase of the invention alone or in combination with other hydrolytic enzymes. The enzyme or the enzyme preparation is added to the pectin-rich biomass and incubated for 1-5 hours at temperatures between 30° C. and 60° C. in concentrations of 10-400 mg/kg, even more particularly 100-300 mg/kg mash. Surprisingly, the degradation of the arabinan sidechains of pectin leads to a higher release of glucose, which results in a higher amount of ethanol after fermentation.

For biogas production agricultural substrates, such as sugar beets, whole plant silages or other arabinan-containing biomass, are added to an anaerobic biogas fermenter. The arabinanase preparation alone or a combination of arabinanase and other NSP-degrading enzymes, such as cellulases, glucanases, xylanases or pectinases, or a combination of arabinanase and a protease, such as an acid stable serine protease, are added to the process regularly, e.g. daily together with the substrate or via a separate supply system. Biogas fermentation takes place at temperatures between 30° C. and 60° C. Hydraulic retention times lie between 30 and 150 days. The amount of added enzyme preparation depends on the amount of substrate fed to the fermenter. Dosages of 1-500 mg/kg substrate, more particularly 10-400 mg/kg substrate, even more particularly 100-300 mg/kg substrate are required.

Surprisingly, the utilization of the arabinanase of the invention alone or in combination with other enzymes, such as cellulases, glucanases, pectinases, xylanases or proteases, leads to a decrease of viscosity and/or to a higher biogas production from pectin-rich substrates under anaerobic conditions.

EXAMPLES

The following examples are meant to illustrate the invention and certain embodiments thereof, without limiting the scope of the invention.
Cloning and Yeast Transformation The arabinanase gene (AABN) was amplified from *A. adeninivorans* genomic DNA with the oligos 5'-CAGGAATTCG GCAGAGGCAC AATGAAGA-3' (SEQ ID NO 03) and 5'-CAGCTGCAGT GGATAGTAGA TGGATGGTAG TA-3' (SEQ ID NO 04) containing restriction sites for EcoRI and PstI, respectively, for subcloning into the pBS-TEF1-PHOS vector (Wartmann, Fems Yeast Research, 2003. 3(2): p. 223-232). The following PCR parameters were chosen: 95° C. for 2 min, 95° C. for 15 sec, 58° C. for 15 sec, 72° C. for 3 min (25 cycles) using the Long PCR Enzyme Mix (Thermo scientific). *E. coli* XI1-Blue cells (recA1 endA1 gyrA96 thi-1 hsdR17 supE44 relA1 lac [F' proAB lacI$^q$ZΔM15 Tn 10(Tet$^r$)]) were used for standard heat transformation (Green, Molecular Cloning: A Laboratory Manual (Fourth Edition). 2012: Cold Spring Harbor Laboratory Press) and grown in LB medium, supplemented with ampicillin (50 µg mL$^{-1}$; AppliChem, Germany) when required for selection. This plasmid served as template to amplify the AABN gene equipped with the constitutive TEF1 promoter with the oligos 5'-CTGCCGCGGC TCGACTTCAA TCT-3' (SEQ ID NO 05) and 5'-CCGCCGCGGC CCCAGCTTGC ATG-3' (SEQ ID NO 06), both containing SacII restriction sites for integration of the construct into the Xplor® 2 expression/transformation vector (Boer, Appl Microbiol Biotechnol, 2009. 84(3): p. 583-594) applying the same PCR conditions as above. After restriction of the resulting plasmid with AscI the AABN expression cassette consisting only of yeast sequences including the ATRP1 selection marker was transformed into the auxotrophic mutant *A. adeninivorans* G1212 [aleu2 atrp1: ALEU2] (Steinborn, J Biotechnol, 2007. 127(3): p. 392-401) according to the Hollenberg transformation procedure (Dohmen, Yeast, 1991. 7(7): p. 691-692).

Based on the amino acid sequence of the arabinanase the estimated molecular weight of the monomer is 42326.16 Daltons. After removal of the putative 23 amino acid secretion signal the mature monomer has a molecular weight of 40094.45 Daltons.

Determination of Enzymatic Activity

The enzyme exhibits endo-arabinanase activity and arabinanofuranosidase activity (EC 3.2.1.99, EC 3.2.1.55).

Endo-arabinanase activity is determined in a photometric assay. Linear arabinan (e.g. arabinan debranched Megazyme P-DBAR) is used as substrate. The enzyme is incubated with the substrate in a buffer having a certain pH (pH 4, 5, 6, 7 or 8) for a certain time (10, 20 or 30 min) at a certain temperature (40, 45, 50, 55 or 60° C.). At the end of the incubation time, the reducing ends of the monosaccharides and oligosaccharides released from the substrate by the enzyme are detected in a redox reaction. In this reaction, the terminal hemiacetal groups of the carbohydrates are oxidized to carboxyl groups, while the added 2-hydroxy-3,5-dinitrobenzoic acid (3,5-dinitrosalicylic acid, DNSA) is reduced, resulting in a photometrically detectable increase in absorption wavelength (bathochromic shift).

The results are compared to a calibration curve, which represents a linear relation between several known arabinose concentrations and the absorption wavelength.

The endo-arabinanase activity within the enzyme preparation was determined using the substrate arabinan debranched (Megazyme) in acetate buffer having a pH of 5.0 at 55° C. The activity was 3000-5000 U g$^{-1}$ preparation depending on the batch. Dry products and enzyme solutions in glycerol (10%) are stable for several months.

Arabinofuranosidase activity is determined using the synthetic substrate p-nitrophenyl-α-L-arabinofuranoside. The enzyme is incubated with the substrate in a buffer having a certain pH (pH 4, 5, 6, 7 or 8) for a certain time (10, 20, 30 or 40 min) at a certain temperature (40° C.). The enzyme releases p-nitrophenol from arabinose, resulting in a photometrically detectable change in absorption at 415 nm. Evaluation occurs using a p-nitrophenol calibration curve.

Arabinofuranosidase activity within the enzyme preparation was determined using the substrate p-nitrophenyl-α-L-arabinofuranoside (1 mM) in citrate buffer having a pH of 5.0 at 40° C. The activity measured was 200-400 U g$^{-1}$ preparation depending on the batch.

Enzymatic activity is determined according to the following formula:

$$Activity = \frac{\text{Volume of enzyme preparation} * \text{dilution} * \Delta OD}{(\text{enzyme preparation} * \text{slope in standard curve} * \text{incubation time})}$$

pH- and Temperature-Stability

Without further formulation, the arabinanase is thermostable up to a temperature of approx. 65° C. Enzymatic activity does not decrease during incubation at 60° C. for 2 hours or during incubation at a pH between 3 and 9 for 48 hours. The enzyme exhibits optimum activity at a temperature between 40° C. and 55° C. and at a pH between 3.5 and 5.5. Temperature optimum was determined in citrate buffer having a pH of 5.5. The pH optimum was determined using acetate buffer (pH 3-6.5), citrate buffer (pH 3.5-7), phosphate buffer (pH 5.5-7.5) and Tris HCl (pH 7-9). The presence of manganese-salts (MnSO$_4$, MnCl$_2$) had positive effects on enzyme activity.

Production of the Arabinanase

To produce the arabinanase, *A. adeninivorans* comprising the arabinanase (AABN) expression cassette is fermented in a fed-batch procedure.

During the batch phase, the following complete medium is used:

|  | (g/L) |
| --- | --- |
| Glycerin | 45 |
| Peptone/yeast extract (2:1) | 60 |
| NH$_4$H$_2$PO$_4$ | 10 |
| K$_2$HPO$_4$/KH$_2$PO$_4$ | 3.5 |
| MgSO$_4$ | 2 |
| KII/Fe/Ca-stock solution | 1 |

During the feed phase, the following two substrates are used:

| Feed 1 | |
| --- | --- |
| Glycerin (400 g C) | 1000 g |
| H$_2$O to | 1 L |

| Feed 2 | |
| --- | --- |
| NH$_4$H$_2$PO$_4$ (20 g N) | 163 g |
| MgSO$_4$ | 30 g |
| KII/Fe/Ca-stock solution | 30 mL |
| H$_2$O to | 500 mL |

Figure 2:
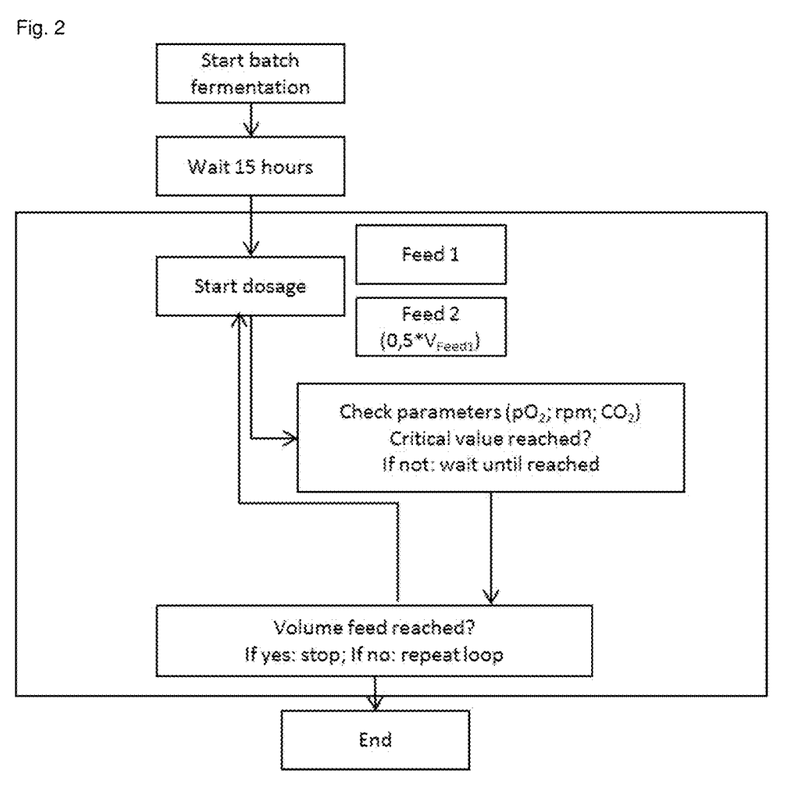
FIG. 2 shows the fed-batch procedure.

After a batch phase of 15 hours, a feeding loop starts (FIG. 2). Fermentation occurs at 40% pO$_2$ and pH 6 for 5 days; pH is adjusted using NaOH (25%) and H$_3$PO$_4$ (10%). At the end of the fermentation process, enzyme activity within the supernatant is 80-90 U g$^{-1}$. Yeast cells are removed in a centrifugation step and the enzyme is purified from the supernatant.

Determination of Plant Biomass Degradation by Hydrolytic Enzymes (Abiotic Experiment)

The degree of plant biomass degradation is determined in relation to time, temperature, pH and enzyme concentration.

50 mg of anhydrous, grinded plant biomass (volatile solids, VS) is provided in reaction tubes (V=2 ml) in 1.4 ml McIlvaine buffer (pH 6). The buffer contains sodium azide (0.02%) and antibiotics (penicillin: 100 I. U. ml$^{-1}$, streptomycin: 0.1 mg ml$^{-1}$), thus preventing growth of microorganisms and ingestion of the sugar moieties released by the test enzymes.

At each experimental timepoint (TP), samples and controls (substrate control and enzyme control) are taken in duplicates (table 1). In addition, glucose standard samples from 0-500 mmol l$^{-1}$ are prepared in McIlvaine-buffer (pH 6).

140 µl water is added to substrate controls, while 140 µl enzyme preparation is added to the samples. Incubation occurs at 40° C. with shaking. Analyzed timepoints are 2 hours (TP 1), 4 hours (TP 2) and 6 hours (TP 3. At each timepoint, the enzymatic reaction is stopped by adding 140 µl NaOH (2M) and 140 µl glucose (30 mM). Samples are then centrifuged for 5 min at 10.000 g.

40 µl of the supernatant is transferred to new reaction tubes. 180 µl of distilled water and 100 µl of dinitrosalicylic acid reagent (DNSA) are added. Samples are heated in a waterbath (10 min, 100° C.) and subsequently cooled on ice. 1 ml of distilled water is added. 250 µl of each sample is transferred to a microtiter plate and analyzed at 530 nm using a photometer.

The amount of glucose equivalents (in mg) released by the enzymatic reaction is determined by comparison of the samples with the glucose standard curve. The degradation activity of the enzyme is determined by the ratio of the released reducing sugars and the deployed substrate (50 mg plant biomass, VS).

TABLE 1

|  | Substrate | Additive |
|---|---|---|
| Sample | 50 mg oTS in 1.4 ml buffer | 140 µl enzyme |
| Substrate control | 50 mg oTS in 1.4 ml buffer | 140 µl water |
| Enzyme control | 1.4 ml buffer | 140 µl enzyme |
| Glucose standard | 1.4 ml buffer | 140 µl glucose solution (5 different concentrations) |

Degradation of Soybean Meal (SBM)

The degradation of soybean meal by the enzyme according to the present invention was analyzed as described in the previous section. In order to relate the results to the present state of the art, the degradation activity of two enzyme preparations established as feed additives (Ronozyme Multigrain and Ronozyme VP) was determined in parallel.

All three enzyme preparations were used at 25.000 ppm, a dose that is approx. 100× higher than the recommended dose for practical applications. The high dose is necessary to obtain a fast and reliable result in the abiotic test procedure.

After 6 hours, the degradation of SBM by Ronozyme Multigrain (containing mainly xylanase and glucanase) was approx. 1%. The degradation of SBM by Ronozyme VP (containing hemicellulases and pectinases) was approx. 8% after 6 hours. The degradation of SBM by the arabinanase according to the present invention was approx. 11% after 6 hours (FIG. 3).

Surprisingly, degradation of SBM by the arabinanase occurred much faster than degradation of SBM by Ronozyme VP. This observation is essential, since passage through the digestive tract takes only a few hours. Thus, the use of arabinanase as feed additive for poultry, pig or other monogastric animals is a significant improvement compared to the use of the currently established feed additives.

The inventors show that by combined addition of the arabinanase according to the present invention and a pectinase product, a synergistic effect can be achieved.

Degradation of Rapeseed Meal (RSM)

The degradation of rapeseed meal by the enzyme according to the present invention was analyzed as described in the previous section. In order to relate the results to the present state of the art, the degradation activity of two enzyme preparations established as feed additives (Ronozyme Multigrain and Ronozyme VP) was determined in parallel.

All three enzyme preparations were used at 25.000 ppm, a dose that is approx. 100× higher than the recommended dose for practical applications. The high dose is necessary to obtain a fast and reliable result in the abiotic test procedure.

The degradation of RSM by Ronozyme Multigrain (containing mainly xylanase and glucanase) was approx. 1%. The degradation of RSM by Ronozyme VP (containing hemicellulases and pectinases) was approx. 7% after 6 hours. The degradation of RSM by the arabinanase according to the present invention was approx. 10% after 6 hours (FIG. 4).

Surprisingly, degradation of RSM by the arabinanase occurred much faster than degradation of RSM by Ronozyme VP. This observation is essential, since passage through the digestive tract takes only a few hours. Thus, the use of arabinanase alone as feed additive for poultry, pig or other monogastric animals is a significant improvement compared to the use of the currently established feed additives.

The inventors show that by combined addition of the arabinanase according to the present invention and a pectinase product, a synergistic effect can be achieved.

Feeding Experiment (Poultry)

In order to assess the efficacy of the arabinanase according to the present invention, broilers were fed with a compound feed diet supplemented with the arabinanase of the invention. At 10 days of age, 96 broilers were divided into 4 groups. All broilers received a basal diet comprising rapeseed meal (35%) and corn (60%). Group A received the basal unsupplemented diet, group B received the basal diet supplemented with an established feed enzyme product (Ronozyme VP) and groups C and D received the basal diet supplemented with the enzyme according to the present invention (Tab. 2). Duration of the feeding experiment was 15 days. During the adaption phase (day 11-14) all groups received the basal diet without any enzyme supplementation. During the experimental phase (day 15-25) all groups received the respective supplemented diets. Feed intake was determined daily throughout the experiment. Body weight was determined upon arrival, on day 14, 21 and 25. Excreta were collected three times daily from day 21 to day 25 in order to assess the apparently metabolizable energy.

TABLE 2

| | Treatment | Enzyme additive | Dosage | Arabinanase activity (U kg$^{-1}$ mixed feed) | Pectinase activity (U kg$^{-1}$ mixed feed) |
|---|---|---|---|---|---|
| A | Negative control | — | — | — | — |
| B | Positive control | Ronozyme VP | 300 ppm | 75 | 3300 |
| C | Test group 1 | Arabinanase | 260 ppm | 1500 | — |
| D | Test group 2 | Arabinanase | 520 ppm | 3000 | — |

Analysis of the experimental diet supplemented with enzymes at the beginning and during the experiment showed that arabinanase activity was detectable and stable throughout the entire experiment.

The following parameters were analyzed:

| | |
|---|---|
| Feed intake | daily |
| Body weight | On day 14, 21 and 25 |
| Apparently metabolizable energy (AME) | Day 21-25 |

It was observed that the group receiving a diet without enzymes (Group A) gained less weight than the positive control group (B) and the two test groups (C and D). Also, group A took in less feed than the other groups (B-D). The feed conversion ratio was best for group D (1.61) and B (1.62), which means that the groups receiving Ronozyme VP or the experimental arabinanase could use the energy present in the diet most efficiently.

This shows that the supplementation of a pectin-rich diet with arabinanase led to a better degradation of the pectin-rich substrate, a decrease of antinutritive effect of rapeseed meal and to strongly positive effects in terms of energy metabolization.

| | Daily weight gain (21-25) (g) mean | Daily feed intake (21-25) (g) mean | Feed conversion ratio (21-25) (g/g) mean |
|---|---|---|---|
| A | 78 | 128 | 1.67 |
| B | 88 | 141 | 1.62 |
| C | 82 | 136 | 1.67 |
| D | 86 | 137 | 1.61 |

Comparison of Arabinanase Activities

The endo-activity of the arabinanase of the invention (*Arxula adeninivorans*) and of a commercial arabinanase from *Aspergillus niger* (Megazyme E-EARAB) were determined in a photometric assay. Debranched arabinan (Megazyme P-DBAR) was used as substrate. The enzymes were incubated with the substrate in a buffer having a pH of 5 for 20 min at 55° C. At the end of the incubation time, the reducing ends of the monosaccharides and oligosaccharides released from the substrate by the enzyme were detected in a redox reaction. In this reaction, the terminal hemiacetal groups of the carbohydrates are oxidized to carboxyl groups, while the added 2-hydroxy-3,5-dinitrobenzoic acid (3,5-dinitrosalicylic acid, DNSA) is reduced, resulting in a photometrically detectable increase in absorption wavelength (bathochromic shift).

Under the described conditions, the activity of the arabinanase of the invention was 5500 U/g and the activity of the commercially available *Aspergillus niger* arabinanase was 645 U/g.

Plant biomass degradation induced by the two enzymes was determined in an abiotic test as explained in detail above. Rapeseed meal and soybean meal were used as insoluble substrates, because these substrates contain high amounts of pectin, which is rich in arabinan side chains.

For the experiment, 12,500 ppm of the arabinanase of *Arxula adeninivorans* and 107,000 ppm *Aspergillus niger* were added to the substrates, which means that equivalent enzyme activity was added to the substrate (68 Units per gram substrate oDM).

Figure 5:
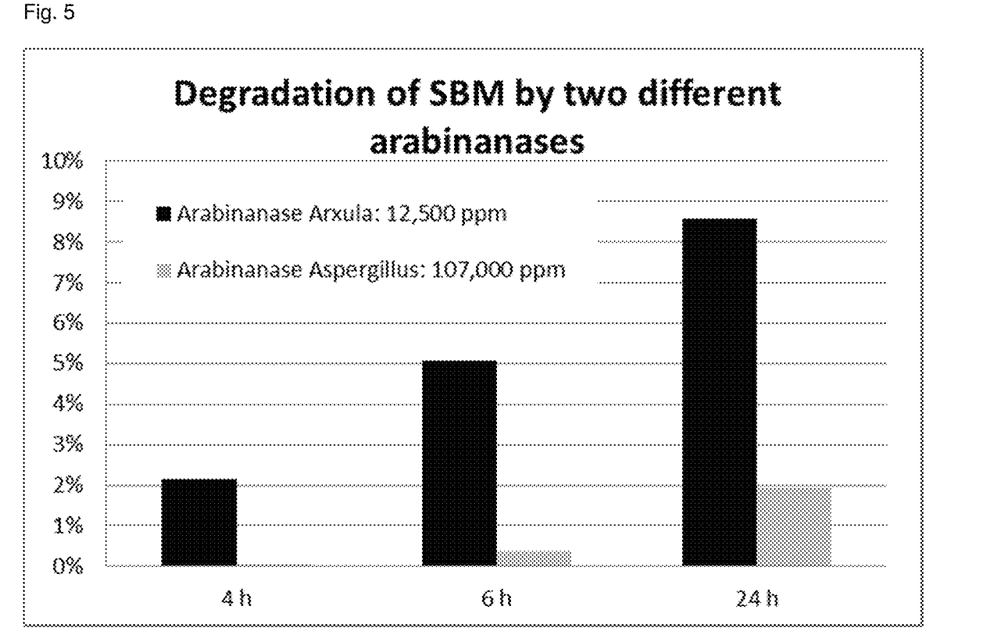
FIG. 5 shows the degradation of soybean meal by the arabinanase according to the present invention and by the arabinananse of *A. niger*.
Figure 6:
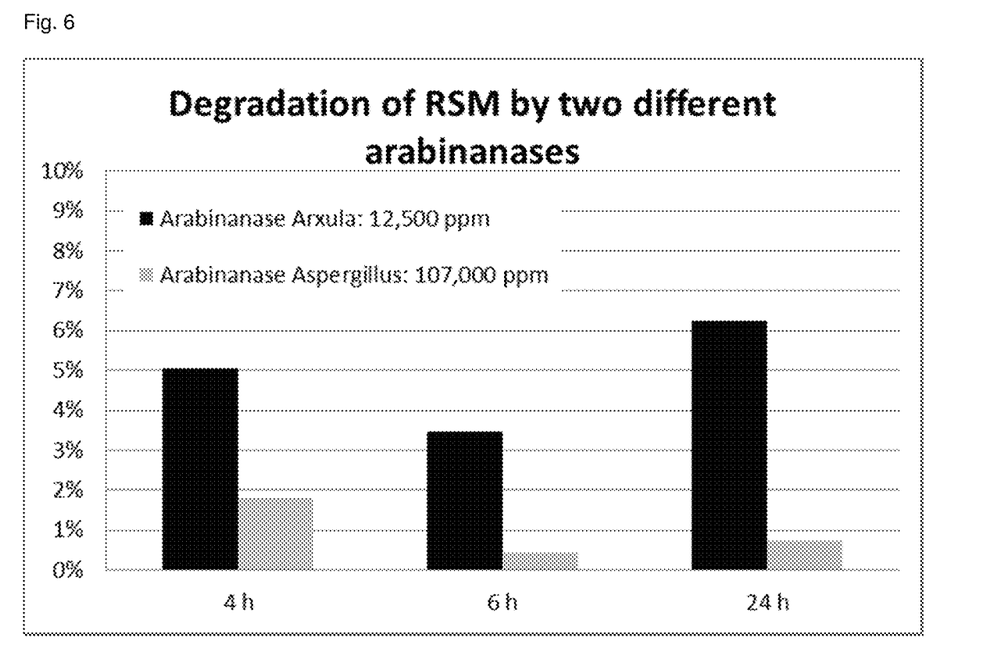
FIG. 6 shows the degradation of rapeseed meal by the arabinanase according to the present invention and by the arabinananse of *A. niger*.

All samples were incubated for 24 hours at 40° C. After 4, 6 and 24 hours the amount of reducing sugars in the supernatant was determined. 9% of the soybean meal was degraded during the first 24 hours using *Arxula* arabinanase, whereas *Aspergillus* arabinanase released only 2% of the carbohydrates (FIG. 5). Also the degradation of rapeseed meal was higher, if *Arxula* arabinanase was used than if *Aspergillus* arabinanase was used (FIG. 6).

It was surprising that the arabinanase of the invention worked much more effective in the degradation of the undissolved plant material than the arabinanase of *Aspergillus niger*, although equivalent levels of endo-arabinanase activity were applied.

Sequences

```
                                                           SEQ ID NO 01
atgaagagcc aattgatcgc tacaattgca accgttgccc tgggctctat gagctctgtg    60
gtggcagcaa agtctaagac cgatgattcc aatacctatg atcgattcag gggactggtt   120
gattccaaca cctatgactt gatgaacaat tcactgggtg aacatatgt ccacactccc    180 aacttgacgg tcattgatac tcccgattgg cctttgccta atccggttat tggagacatt   240
gtgccctggg gaggtgttca ccttcatgac ccttctatta tcaagcacaa tgggtattac   300
tactctttca ccacccacaa cttgattgga atttccaagg ctccatccat gtttggtccc   360
tggcaaaaga ttggaagtgt gttggaggag tccagtatca ttaacagtac tggaagcaca   420
gatccttggg ccctgatgt gcaaaaggtt ggagacacat tctactgcta ctacgccgtc    480
tcctcctttg gaagcccaa gtcgtcaatt ggactagcta cgtccaagac gcttgagccc    540
ggttcttgga ccgaccacg agaggttatc agttctggtc ccaatgctcc ttaccctctc   600
aatgactcca atgccattga cgctaacctg cttgttgtgg agaatggcaa ttccgttcag   660
gaggcttatc tgctgtgggg gtctttctgg tctaacattt ggcagatcaa gctcaacaat   720
gatctgaccg tgccagacaa tgccattgcc aatgctgtcc agctcgccta cgacggcaca   780
attgacactc atccagttga aggtgcttat ctccacaagg ccagcaatgg atactactac   840
ttgtttgtgt ccaatggagt gtgctgtgga tacgacgctg ctctgcctga tgctggccga   900
```

-continued

```
gagtataaga tcttggtcgg tcgttcaaag tctccatctg gtcctttcct tgacaagaac    960
ggggtcgaca tggccaaggg cggtggatct cgaatctatg gttctcatgg aattgtctat   1020
ggacctggag acagggagt gtttactgat gatgacggac aggatatcat ttactaccac   1080
tatgttgatc tgagagtcag tcttgccgat gatgacaagc gtctgggatg aactatctc   1140 aagtacgaag acggttggcc aaaactcgtt tag                               1173
```

SEQ ID NO 02

MKSQLIATIATVALGSMSSVVAAKSKTDDSNTYDRFRGLVDSNTYDLMNNSLGGTYVHTPN

LTVIDTPDWPLPNPVIGDIVPWGGVHLHDPSIIKHNGYYYSFTTHNLIGISKAPSMFGPWQKI

GSVLEESSIINSTGSTDPWAPDVQKVGDTFYCYYAVSSFGSPKSSIGLATSKTLEPGSWTDH

GEVISSGPNAPYPLNDSNAIDANLLVVENGNSVQEAYLLWGSFWSNIWQIKLNNDLTVPDNA

IANAVQLAYDGTIDTHPVEGAYLHKASNGYYYLFVSNGVCCGYDAALPDAGREYKILVGRSK

SPSGPFLDKNGVDMAKGGGSRIYGSHGIVYGPGGQGVFTDDDGQDIIYYHYVDLRVSLADD

DKRLGWNYLKYEDGWPKLV

---

We claim:

1. A method for degradation of a pectin-rich plant biomass, comprising:
    providing a composition consisting essentially of an isolated enzyme having arabinase activity to a pectin-rich plant biomass, and
    reacting said composition and said plant biomass at a temperature of between 35° C. and 60° C.;
    wherein said arabinanase activity comprises the activity of endohydrolysis of (1-5)-α-arabinofuranosidic linkages in (1-5)-α L arabinans (EC 3.2.1.99);
    wherein the enzyme has an amino acid sequence at least 99% identical to SEQ ID NO 02.

2. The method of claim 1, wherein the plant biomass is an animal feed and wherein reacting said composition and thereby degrading the plant biomass, occurs in a digestive tract of an animal.

3. The method of claim 1, wherein the enzyme additionally catalyses hydrolysis of (1-3)-α- and (1,2)-α-arabinofuranosidic linkages at the non-reducing end of α-L-arabinans or α-L-arabinose-oligomers.

4. The method of claim 1, wherein the enzyme exhibits optimum activity at a temperature between 40° C.-55° C., and at a pH between 3.5-5.5.

5. The method of claim 1, wherein the pectin-rich plant biomass is a liquid preparation selected from apple juice, pear juice, grape juice, orange juice, lemon juice, tomato juice, and carrot, and wherein the method further comprises contacting said liquid preparation with said enzyme.

6. The method of claim 1, wherein the pectin-rich plant biomass is a substrate for biofuel production.

7. The method of claim 1, wherein the pectin-rich plant biomass is provided in a compound animal feed, and wherein the degradation occurs in the digestive tract of an animal.

8. The method of claim 1, wherein the pectin-rich plant biomass, is selected from the group consisting of beets, oilseeds, and legumes.

9. The method of claim 1, wherein the pectin-rich plant biomass further comprises a starch.

10. The method of claim 1, wherein a concentration of the enzyme is 1-500 mg/kg of the pectin-rich plant biomass.

11. The method of claim 1, further comprising providing an additional isolated enzyme selected from the group consisting of phytase, protease and an NSP-degrading enzyme, at a concentration of 1-500 mg/kg of the pectin-rich plant biomass.

12. The method of claim 7, wherein the animal feed is feed for monogastric animals.

13. The method of claim 6, wherein the substrate for biofuel production is a substrate for biogas and bioethanol production.

14. The method of claim 8, wherein the beets are sugar beet, wherein the oilseeds are selected from rapeseed and soy, and wherein the legumes are lupines.

\* \* \* \* \*

SEQUENCE LISTING

<160> NUMBER OF SEQ ID NOS: 6

<210> SEQ ID NO 1
<211> LENGTH: 1173
<212> TYPE: DNA
<213> ORGANISM: Arxula adeninivorans

<400> SEQUENCE: 1

```
atgaagagcc aattgatcgc tacaattgca accgttgccc tgggctctat gagctctgtg     60
gtggcagcaa agtctaagac cgatgattcc aatacctatg atcgattcag gggactggtt    120
gattccaaca cctatgactt gatgaacaat tcactgggtg aacatatgt ccacactccc     180 aacttgacgg tcattgatac tcccgattgg cctttgccta atccggttat tggagacatt    240
gtgccctggg gaggtgttca ccttcatgac ccttctatta tcaagcacaa tgggtattac    300
tactctttca ccacccacaa cttgattgga atttccaagg ctccatccat gtttggtccc    360
tggcaaaaga ttggaagtgt gttggaggag tccagtatca ttaacagtac tggaagcaca    420
gatccttggg cccctgatgt gcaaaaggtt ggagacacat tctactgcta ctacgccgtc    480
tcctcctttg gaagccccaa gtcgtcaatt ggactagcta cgtccaagac gcttgagccc    540
ggttcttgga ccgaccacgg agaggttatc agttctggtc ccaatgctcc ttaccctctc    600
aatgactcca atgccattga cgctaaccctg cttgttgtgg agaatggcaa ttccgttcag    660
gaggcttatc tgctgtgggg gtcttttctgg tctaacattt ggcagatcaa gctcaacaat    720
gatctgaccg tgccagacaa tgccattgcc aatgctgtcc agctcgccta cgacggcaca    780
attgacactc atccagttga aggtgcttat ctccacaagg ccagcaatgg atactactac    840
ttgtttgtgt ccaatggagt gtgctgtgga tacgacgctg ctctgcctga tgctggccga    900
gagtataaga tcttggtcgg tcgttcaaag tctccatctg gtcctttcct tgacaagaac    960
ggggtcgaca tggccaaggg cggtggatct cgaatctatg gttctcatgg aattgtctat   1020
ggacctggag acagggagt gtttactgat gatgacggac aggatatcat ttactaccac   1080
tatgttgatc tgagagtcag tcttgccgat gatgacaagc gtctgggatg aactatctc   1140 aagtacgaag acggttggcc aaaactcgtt tag                               1173
```

```
<210> SEQ ID NO 2
<211> LENGTH: 390
<212> TYPE: PRT
<213> ORGANISM: Arxula adeninivorans

<400> SEQUENCE: 2

Met Lys Ser Gln Leu Ile Ala Thr Ile Ala Thr Val Ala Leu Gly Ser
1               5                   10                  15

Met Ser Ser Val Val Ala Ala Lys Ser Lys Thr Asp Asp Ser Asn Thr
            20                  25                  30

Tyr Asp Arg Phe Arg Gly Leu Val Asp Ser Asn Thr Tyr Asp Leu Met
        35                  40                  45

Asn Asn Ser Leu Gly Gly Thr Tyr Val His Thr Pro Asn Leu Thr Val
    50                  55                  60

Ile Asp Thr Pro Asp Trp Pro Leu Pro Asn Pro Val Ile Gly Asp Ile
65                  70                  75                  80

Val Pro Trp Gly Gly Val His Leu His Asp Pro Ser Ile Ile Lys His
                85                  90                  95

Asn Gly Tyr Tyr Tyr Ser Phe Thr Thr His Asn Leu Ile Gly Ile Ser
            100                 105                 110

Lys Ala Pro Ser Met Phe Gly Pro Trp Gln Lys Ile Gly Ser Val Leu
        115                 120                 125

Glu Glu Ser Ser Ile Ile Asn Ser Thr Gly Ser Thr Asp Pro Trp Ala
130                 135                 140

Pro Asp Val Gln Lys Val Gly Asp Thr Phe Tyr Cys Tyr Tyr Ala Val
145                 150                 155                 160

Ser Ser Phe Gly Ser Pro Lys Ser Ile Gly Leu Ala Thr Ser Lys
                165                 170                 175

Thr Leu Glu Pro Gly Ser Trp Thr Asp His Gly Glu Val Ile Ser Ser
            180                 185                 190

Gly Pro Asn Ala Pro Tyr Pro Leu Asn Asp Ser Asn Ala Ile Asp Ala
        195                 200                 205

Asn Leu Leu Val Val Glu Asn Gly Asn Ser Val Gln Glu Ala Tyr Leu
    210                 215                 220

Leu Trp Gly Ser Phe Trp Ser Asn Ile Trp Gln Ile Lys Leu Asn Asn
225                 230                 235                 240

Asp Leu Thr Val Pro Asp Asn Ala Ile Ala Asn Ala Val Gln Leu Ala
                245                 250                 255

Tyr Asp Gly Thr Ile Asp Thr His Pro Val Glu Gly Ala Tyr Leu His
            260                 265                 270

Lys Ala Ser Asn Gly Tyr Tyr Leu Phe Val Ser Asn Gly Val Cys
        275                 280                 285

Cys Gly Tyr Asp Ala Ala Leu Pro Asp Ala Gly Arg Glu Tyr Lys Ile
    290                 295                 300

Leu Val Gly Arg Ser Lys Ser Pro Ser Gly Pro Phe Leu Asp Lys Asn
305                 310                 315                 320

Gly Val Asp Met Ala Lys Gly Gly Ser Arg Ile Tyr Gly Ser His
                325                 330                 335

Gly Ile Val Tyr Gly Pro Gly Gln Gly Val Phe Thr Asp Asp
            340                 345                 350

Gly Gln Asp Ile Ile Tyr Tyr His Tyr Val Asp Leu Arg Val Ser Leu
        355                 360                 365

Ala Asp Asp Asp Lys Arg Leu Gly Trp Asn Tyr Leu Lys Tyr Glu Asp
370                 375                 380
```

```
Gly Trp Pro Lys Leu Val
385                 390

<210> SEQ ID NO 3
<211> LENGTH: 28
<212> TYPE: DNA
<213> ORGANISM: Artificial Sequence
<220> FEATURE:
<223> OTHER INFORMATION: primer comprising restrction site for
      amplification of the arabinase (AABN) gene from A. adeninivorans
      genomic DNA

<400> SEQUENCE: 3
caggaattcg gcagaggcac aatgaaga                                    28

<210> SEQ ID NO 4
<211> LENGTH: 32
<212> TYPE: DNA
<213> ORGANISM: Artificial Sequence
<220> FEATURE:
<223> OTHER INFORMATION: primer comprising restriction site for
      amplification of the arabinanase gene (AABN) from A. adeninivorans
      genomic DNA

<400> SEQUENCE: 4
cagctgcagt ggatagtaga tggatggtag ta                               32

<210> SEQ ID NO 5
<211> LENGTH: 23
<212> TYPE: DNA
<213> ORGANISM: Artificial Sequence
<220> FEATURE:
<223> OTHER INFORMATION: cloning primer comprising restriction site

<400> SEQUENCE: 5
ctgccgcggc tcgacttcaa tct                                         23

<210> SEQ ID NO 6
<211> LENGTH: 23
<212> TYPE: DNA
<213> ORGANISM: Artificial Sequence
<220> FEATURE:
<223> OTHER INFORMATION: cloning primer comprising restriction site

<400> SEQUENCE: 6
ccgccgcggc cccagcttgc atg                                         23
```